US012544019B2

(12) United States Patent
DeFreitas et al.

(10) Patent No.: US 12,544,019 B2
(45) Date of Patent: Feb. 10, 2026

(54) X-RAY MAMMOGRAPHY AND/OR BREAST TOMOSYNTHESIS USING A COMPRESSION PADDLE WITH AN INFLATABLE JACKET ENHANCING IMAGING AND IMPROVING PATIENT COMFORT

(71) Applicant: Hologic, Inc., Marlborough, MA (US)

(72) Inventors: Kenneth F. DeFreitas, Patterson, NY (US); Ian Shaw, Swampscott, MA (US); Timothy R. Stango, Sandy Hook, CT (US)

(73) Assignee: Hologic, Inc., Marlborough, MA (US)

(*) Notice: Subject to any disclaimer, the term of this patent is extended or adjusted under 35 U.S.C. 154(b) by 46 days.

(21) Appl. No.: 18/760,495

(22) Filed: Jul. 1, 2024

(65) Prior Publication Data

US 2025/0032064 A1 Jan. 30, 2025

Related U.S. Application Data

(63) Continuation of application No. 18/130,095, filed on Apr. 3, 2023, now Pat. No. 12,059,278, which is a continuation of application No. 15/595,440, filed on May 15, 2017, now abandoned, which is a continuation of application No. 15/147,800, filed on May 5, 2016, now Pat. No. 9,649,075, which is a continuation of application No. 13/679,446, filed on Nov. 16, 2012, now Pat. No. 9,332,947.

(60) Provisional application No. 61/561,620, filed on Nov. 18, 2011.

(51) Int. Cl.

| | |
|---|---|
| ***A61B 6/00*** | (2024.01) |
| ***A61B 6/02*** | (2006.01) |
| ***A61B 6/04*** | (2006.01) |
| ***A61B 6/50*** | (2024.01) |

(52) U.S. Cl.

CPC ................ *A61B 6/04* (2013.01); *A61B 6/025* (2013.01); *A61B 6/0414* (2013.01); *A61B 6/502* (2013.01)

(58) Field of Classification Search

CPC .............................. A61B 6/0414; A61B 6/502

See application file for complete search history.

(56) References Cited

U.S. PATENT DOCUMENTS

| | | | |
|---|---|---|---|
| 3,578,971 | A | 5/1971 | Lasky |
| 3,971,950 | A | 7/1976 | Evans et al. |
| 4,496,557 | A | 1/1985 | Malen |
| 4,567,899 | A | 2/1986 | Kamens et al. |
| 4,943,986 | A | 7/1990 | Barbarisi |
| 4,962,515 | A | 10/1990 | Kopans |

(Continued)

FOREIGN PATENT DOCUMENTS

| | | |
|---|---|---|
| AU | 2008201638 | 5/2008 |
| CN | 1586399 | 3/2005 |

(Continued)

OTHER PUBLICATIONS

Chinese Office Action in Application 201480031539.1, mailed Mar. 26, 2019, 11 pages. (with English translation).

(Continued)

*Primary Examiner* — Dani Fox

(74) *Attorney, Agent, or Firm* — Merchant & Gould P.C.

(57) ABSTRACT

A system and method using an inflatable jacket over the compression paddle of a mammography and/or tomosynthesis system to enhance imaging and improve patient comfort in x-ray breast imaging.

20 Claims, 3 Drawing Sheets

(56) References Cited

U.S. PATENT DOCUMENTS 5,040,198 A 8/1991 Hixson, Sr.
5,051,904 A 9/1991 Griffith
5,107,255 A 4/1992 Shiraishi
5,109,398 A 4/1992 Hunt
5,199,056 A 3/1993 Darrah
5,257,121 A 10/1993 Steinberg
5,359,637 A 10/1994 Webber
5,398,272 A 3/1995 Bouscary et al.
5,474,072 A 12/1995 Shmulewitz
5,506,877 A 4/1996 Niklason
5,553,111 A 9/1996 Moore et al.
D376,012 S 11/1996 Hixson, Sr.
5,706,327 A 1/1998 Adamkowski
6,049,583 A 4/2000 Galkin
6,122,542 A 9/2000 Lee
6,289,235 B1 9/2001 Webber
6,577,702 B1 6/2003 Lebovic et al.
6,587,578 B2 7/2003 Godik et al.
6,647,092 B2 11/2003 Eberhard
6,682,484 B1 1/2004 Entrekin et al.
6,765,984 B2 7/2004 Higgins et al.
6,850,590 B2 2/2005 Galkin
6,968,033 B2 11/2005 Lebovic et al.
6,974,255 B1 12/2005 Hixson, Sr.
6,975,701 B2 12/2005 Galkin
7,123,684 B2 10/2006 Jing et al.
7,203,348 B1 4/2007 Karrsemeijer
7,245,694 B2 7/2007 Jing et al.
7,319,735 B2 1/2008 DeFreitas
7,430,272 B2 9/2008 Jing et al.
7,489,761 B2 2/2009 DeFreitas et al.
7,505,555 B2 3/2009 Hermann et al.
7,512,211 B2 3/2009 Galkin
7,583,786 B2 9/2009 Jing et al.
7,634,049 B2 * 12/2009 Galkin .................. A61B 6/502 378/37
7,639,780 B2 12/2009 Minyard
7,656,993 B2 2/2010 Hoernig
7,702,142 B2 4/2010 Ren et al.
7,742,558 B2 6/2010 Mertelmeier et al.
7,760,853 B2 7/2010 Jing et al.
7,792,244 B2 9/2010 DeFreitas et al.
7,822,457 B2 10/2010 Lokhandwalla et al.
7,831,296 B2 11/2010 Defreitas
7,869,563 B2 1/2011 Defreitas et al.
8,155,421 B2 4/2012 Ren et al.
8,175,219 B2 5/2012 DeFreitas et al.
8,787,522 B2 7/2014 Smith et al.
9,050,009 B2 6/2015 Den Heeten
9,226,718 B1 1/2016 Baxley
9,332,947 B2 5/2016 DeFreitas et al.
9,498,180 B2 11/2016 Ren et al.
9,649,075 B2 5/2017 DeFreitas et al.
9,743,997 B2 8/2017 Grimbergen
9,782,135 B2 10/2017 Stango et al.
9,826,950 B2 11/2017 Den Heeten
10,603,002 B2 3/2020 Stango
10,888,292 B2 1/2021 Stango
11,064,956 B2 7/2021 DeFreitas
11,259,759 B2 3/2022 Stango et al.
11,622,736 B2 4/2023 Defreitas
11,633,164 B2 4/2023 Stango
11,672,493 B2 6/2023 Banks
11,707,244 B2 7/2023 Laviola
11,950,941 B2 4/2024 Stango
11,992,352 B2 5/2024 Stango
2001/0038861 A1 11/2001 Hsu
2002/0032373 A1 3/2002 Godik et al.
2002/0061090 A1 5/2002 Lindstrom
2003/0007597 A1 1/2003 Higgins et al.
2003/0007598 A1 1/2003 Wang et al.
2003/0099325 A1 5/2003 Galkin
2003/0174807 A1 9/2003 Lebovic
2004/0066882 A1 4/2004 Eberhard
2004/0066884 A1 4/2004 Claus
2004/0066904 A1 4/2004 Eberhard
2004/0094167 A1 5/2004 Brady
2004/0156472 A1 8/2004 Galkin
2004/0218727 A1 11/2004 Shoenfeld
2005/0008117 A1 1/2005 Livingston
2005/0063509 A1 3/2005 DeFreitas et al.
2005/0113681 A1 5/2005 DeFreitas et al.
2005/0113683 A1 5/2005 Lokhandwalla et al.
2005/0113863 A1 5/2005 Ramzipoor et al.
2006/0050844 A1 3/2006 Galkin
2006/0165215 A1 7/2006 Galkin
2007/0081625 A1 4/2007 Sendai
2007/0223652 A1 9/2007 Galkin
2007/0242794 A1 10/2007 Stanton
2007/0280412 A1 12/2007 Defreitas et al.
2008/0043904 A1 2/2008 Hoernig
2008/0080668 A1 4/2008 Kashiwagi
2008/0087830 A1 4/2008 Kashiwagi
2008/0181361 A1 7/2008 Eldered et al.
2008/0240345 A1 10/2008 Galkin
2008/0242979 A1 10/2008 Fischer et al.
2008/0247508 A1 10/2008 Harrington
2009/0003519 A1 1/2009 DeFreitas et al.
2009/0135997 A1 5/2009 DeFreitas
2009/0175408 A1 7/2009 Goodsitt et al.
2009/0262887 A1 10/2009 Lordache et al.
2009/0268865 A1 10/2009 Ren
2009/0304146 A1 12/2009 Ramsauer
2009/0324049 A1 12/2009 Kontos et al.
2010/0046698 A1 2/2010 Lebovic et al.
2010/0049093 A1 2/2010 Galkin
2010/0111249 A1 5/2010 Mertelmeir et al.
2010/0329418 A1 12/2010 Blevis
2011/0058724 A1 3/2011 Claus
2011/0064190 A1 3/2011 Ruimi
2011/0087098 A1 4/2011 Fischer et al.
2011/0257919 A1 10/2011 Reiner
2012/0033868 A1 2/2012 Ren
2012/0051522 A1 3/2012 Nishino
2012/0114095 A1 5/2012 Smith et al.
2012/0150034 A1 6/2012 DeFreitas
2012/0277625 A1 11/2012 Nakayama
2013/0012837 A1 1/2013 Krogure
2013/0028499 A1 1/2013 Tsujii
2013/0051520 A1 2/2013 Ramsauer
2013/0129039 A1 5/2013 DeFreitas et al.
2013/0272493 A1 10/2013 Otokuni
2014/0107493 A1 4/2014 Yuen
2014/0296701 A1 10/2014 Hancu et al.
2014/0328458 A1 11/2014 Erhard et al.
2014/0378816 A1 12/2014 Oh
2015/0272682 A1 10/2015 Sheng
2015/0282770 A1 10/2015 Klanian et al.
2015/0297163 A1 10/2015 Kim
2016/0066875 A1 3/2016 Jacob et al.
2016/0081633 A1 3/2016 Stango et al.
2016/0166234 A1 6/2016 Zhang
2016/0183889 A1 6/2016 Matsuura
2016/0242707 A1 8/2016 Defreitas et al.
2017/0055930 A1 3/2017 Hagiwara
2017/0251991 A1 9/2017 Wang
2017/0340303 A1 11/2017 Stango
2017/0347976 A1 12/2017 DeFreitas et al.
2018/0125437 A1 5/2018 Stango et al.
2018/0165840 A1 6/2018 Bernard
2018/0184999 A1 7/2018 Davis
2020/0069274 A1 3/2020 Stango
2020/0178926 A1 6/2020 Kshirsagar
2020/0196971 A1 6/2020 Laviola
2020/0359974 A1 11/2020 DeFreitas
2020/0359975 A1 11/2020 Banks
2020/0390405 A1 12/2020 DeFreitas
2021/0015435 A1 1/2021 DeFreitas
2021/0113169 A1 4/2021 Stango
2021/0228165 A1 7/2021 Defreitas
2022/0087627 A1 3/2022 Stango
2023/0233161 A1 7/2023 DeFreitas
2023/0346329 A1 11/2023 Stango
2023/0355190 A1 11/2023 DeFreitas

(56) References Cited

U.S. PATENT DOCUMENTS

| | | | |
|---|---|---|---|
| 2023/0363726 | A1 | 11/2023 | Banks |
| 2024/0180509 | A1 | 6/2024 | Defreitas |
| 2024/0245364 | A1 | 7/2024 | Stango |
| 2024/0341710 | A1 | 10/2024 | Stango |

FOREIGN PATENT DOCUMENTS

| | | | |
|---|---|---|---|
| CN | 1738573 | | 2/2006 |
| CN | 1810209 | | 8/2006 |
| CN | 101766490 | A | 7/2010 |
| CN | 102196772 | | 9/2011 |
| CN | 102448375 | | 5/2012 |
| CN | 102781328 | | 11/2012 |
| CN | 103281961 | | 9/2013 |
| CN | 104066374 | | 9/2014 |
| CN | 105286904 | | 2/2016 |
| CN | 105637562 | | 6/2016 |
| CN | 105769236 | | 7/2016 |
| CN | 107170031 | | 9/2017 |
| CN | 107518908 | | 12/2017 |
| CN | 109893158 | | 6/2019 |
| CN | 211432963 | | 9/2020 |
| CN | 112004473 | | 11/2020 |
| CN | 115348838 | | 11/2022 |
| DE | 10 2017 207147 | | 10/2018 |
| EP | 955886 | | 11/1999 |
| EP | 1004274 | A1 | 5/2000 |
| EP | 2716228 | | 4/2014 |
| EP | 2341832 | B1 | 7/2014 |
| EP | 2943125 | B1 | 9/2018 |
| GB | 2545641 | | 6/2017 |
| JP | S53-103672 | | 8/1978 |
| JP | H03-86154 | | 4/1991 |
| JP | H05-076409 | U | 3/1992 |
| JP | 2003-525681 | | 9/2003 |
| JP | 2004-261306 | | 9/2004 |
| JP | 2005-523043 | | 8/2005 |
| JP | 2006-212427 | | 8/2006 |
| JP | 2007-135704 | | 6/2007 |
| JP | 2008-518722 | A | 6/2008 |
| JP | 2009-526618 | A | 7/2009 |
| JP | 2009-219656 | | 10/2009 |
| JP | 8-215172 | | 3/2010 |
| JP | 2011-072667 | | 4/2011 |
| JP | 2011-206436 | | 10/2011 |
| JP | 2011-206438 | | 10/2011 |
| JP | 2011-206439 | | 10/2011 |
| JP | 2011-212111 | | 10/2011 |
| JP | 2011-224351 | | 11/2011 |
| JP | 2011-250842 | | 12/2011 |
| JP | 2012-125536 | | 7/2012 |
| JP | 2012-170718 | | 9/2012 |
| JP | 2012-228404 | | 11/2012 |
| JP | 2013017491 | | 1/2013 |
| JP | 2014-068884 | | 4/2014 |
| JP | 2014-068885 | | 4/2014 |
| JP | 2015-027382 | | 2/2015 |
| JP | 2016-022061 | | 2/2016 |
| JP | 2016-517740 | | 6/2016 |
| KR | 10-2011-0089446 | | 8/2011 |
| KR | 10-2014-0058066 | | 5/2014 |
| NL | 2020910 | B1 | 11/2019 |
| WO | 2004/030523 | | 4/2004 |
| WO | 2006/050466 | | 5/2006 |
| WO | 2010/028208 | | 3/2010 |
| WO | 2010/102087 | | 9/2010 |
| WO | 2011/058730 | | 5/2011 |
| WO | 2014059366 | | 4/2014 |
| WO | 2014/074602 | | 5/2014 |
| WO | 2014/176445 | | 10/2014 |
| WO | 2015/054518 | | 4/2015 |
| WO | 2016/073445 | | 5/2016 |
| WO | 2018/067005 | | 4/2018 |
| WO | 2018/089118 | | 5/2018 |
| WO | 2018/170265 | | 9/2018 |
| WO | 2019/004821 | | 1/2019 |
| WO | 2019/088826 | | 5/2019 |
| WO | 2019/227051 | | 11/2019 |
| WO | 20190227042 | | 11/2019 |
| WO | 20190227044 | | 11/2019 |

OTHER PUBLICATIONS

Digital Clinical Reports, Tomosynthesis (GE Brochure 98-5493, Nov. 1998), 8 pgs.

European extended Search Report in Application 19185526.1, mailed Oct. 8, 2019, 7 pages.

European Search Report in Application 14727133.2, mailed Feb. 27, 2017, 9 pgs. (client sent this to US on Mar. 2, 17—corresponds to 4USWO).

European Supplementary Search Report, in Application 12849236.0, mailed May 13, 2013, 2 pgs.

Grant, D.G., "Tomosynthesis: a three-dimensional imaging technique", IEEE Trans. Biomed. Engineering, vol. BME-19, #1, (Jan. 1972), pp. 20-28.

Japanese Office Action in Application 2018-173823, mailed Jul. 11, 2019, 4 pages. (with English translation).

PCT International Search Report and Written opinion in International Application PCT/US2012/065546, mailed Feb. 5, 2013, 10 pgs.

PCT International Search Report and Written Opinion in International Patent Application PCT/US2014/035334 mailed Nov. 12, 2014, 16 pgs.

PCT International Search Report in International Application PCT/US2012/065546, mailed Feb. 5, 2013, 4 pgs.

U.S. Appl. No. 60/628,516 entitled "Matching geometry generation and display of mammograms and tomosynthesis images", filed Nov. 15, 2004, 20 pgs.

* cited by examiner

X-RAY MAMMOGRAPHY AND/OR BREAST TOMOSYNTHESIS USING A COMPRESSION PADDLE WITH AN INFLATABLE JACKET ENHANCING IMAGING AND IMPROVING PATIENT COMFORT

CROSS-REFERENCE TO RELATED APPLICATIONS

This application is a continuation of U.S. patent application Ser. No. 18/130,095, now U.S. Pat. No. 12,059,278, filed Apr. 3, 2023, which is a continuation of U.S. patent application Ser. No. 15/595,440, now abandoned, filed May 15, 2017, which is a continuation of U.S. patent application Ser. No. 15/147,800, now U.S. Pat. No. 9,649,075, filed May 5, 2016, which is a continuation of U.S. patent application Ser. No. 13/679,446, now U.S. Pat. No. 9,332,947, filed Nov. 16, 2012, which claims priority to U.S. Provisional Patent Application No. 61/561,620, filed Nov. 18, 2011, the entire disclosures of which are incorporated herein by reference in their entireties.

FIELD

This patent specification pertains to mammography and/or breast tomosynthesis using an inflatable compression paddle jacket that improves patient comfort and imaging results.

BACKGROUND AND SUMMARY OF THE DISCLOSURE

A significant patient concern in mammography and breast tomosynthesis is the discomfort the patient may feel when the breast is compressed, typically between two rigid plastic surfaces, with sufficient force to immobilize the breast and spread out the breast tissues for x-ray imaging. Another significant challenge is to ensure that the imaged field include the desired amount of breast tissue. The reasons for using compression include: (1) to make the breast thinner in the direction of x-ray flux and thereby reduce patient radiation exposure from the level required to image the thicker parts of a breast that is not compressed; (2) to make the breast more uniform in thickness in the direction of x-ray flux and thereby facilitate more uniform exposure at the image plane over the entire breast image; (3) to immobilize the breast during the x-ray exposure and thereby reduce image blurring; and (4) to bring breast tissues out from the chest wall into the imaging exposure field and thus image more tissue. As the breast is being compressed, typically a technician manipulates the breast to position it appropriately and counter the tendency that compression has of pushing breast tissue toward the chest wall and out of the image field.

Standard compression methods for mammography and tomosynthesis use a movable, rigid clear plastic compression paddle. The breast is placed on a breast platform that typically is flat, and the paddle is then compressed onto the breast, usually while a technician or other health professional is holding the breast in place and perhaps manipulates the breast to ensure proper tissue coverage in the image receptor's field of view and to help spread the breast.

One reason for discomfort that the patient may feel is that the compression force is non-uniformly distributed throughout the breast. It is concentrated at the thickest portion of the breast, usually near the chest wall, at or near the lower front edge of the compression paddle and the upper front corner of the breast platform. The anterior portion of the breast, such as near the nipple, may receive less compressive force, or no compression force. The paddle may not even contact this portion of the breast. (The terms front, lower and upper pertain to using a CC imaging orientation, with the patient facing the front of the imaging system, although it should be understood that other imaging orientations, including MLO, are used with the same equipment and these terms need to be adjusted accordingly.)

Some systems improve patient comfort by providing compression paddles that tilt as the breast is being compressed. A tilting paddle arrangement is available in various paddle sizes from Lorad of Danbury, CT, a division of the assignee hereof, Hologic, Inc. of Bedford, MA, under the trade name F.A.S.T. (of FAST). This tilting paddle provides more uniform compression across the breast, and more comfortable breast examinations.

Other methods for improving patient comfort have been proposed and some have been in clinical use to improve patient comfort. One is the use of relatively thin foam pads that are placed above and/or below the breast. The pad deforms to some extent during the compression procedure and may provide improved comfort by spreading out the pressure to a greater extent than using a hard-surfaced paddle and/or breast platform alone. One such pad system is discussed in commonly owned U.S. Pat. Nos. 6,968,033, 6,765,984, 6,577,702, and 7,505,555, and published U.S. patent application US 2003/0007597 A1. Another pad system is proposed in U.S. Pat. Nos. 6,850,590 and 6,975,701 and published U.S. patent applications US 2006/0050844 A1, US 2004.0156472 A1 and US 2003/0099325 A1, all naming as the inventor Benjamin M. Galkin. Such pads are not transparent to visible light. As a result, if such a pad is between the breast and the compression paddle, the breast will not be visible through the paddle, and this can impair the technician's effort to position and manipulate the breast during compression. The pad needs to be made of fairly dense thin form, so as to provide meaningful deformability when compressed under or above the breast. If the foam pad slips during positioning and as a result does not cover the entire imaging field, an edge of the pad may cause image artifacts.

Another system for improving patient comfort has been proposed for a different purpose—to immobilize the breast during biopsy—by Scientific Biopsy (www.sbiopsy.com). It is understood to use a soft, trough-shaped support to cradle the breast and a flexible band that wraps over the breast to impose a holding force. A thin plastic sheet compressing a breast for ultrasound examination rather than for x-ray imaging is proposed in published patent application US 2003/0007598 A1 (see, e.g., FIG. 7 and paragraph [0115]) but no teaching could be found that the material is transparent to visible light or that the arrangement is useful for x-ray imaging or with a flat breast platform. U.S. Pat. No. 6,682,484 discusses the use of a polymeric membrane stretched under tension to restrain the breast during sonographic and/or x-ray imaging. U.S. Pat. No. 7,822,457 discusses the use of tensioned membrane to compress the breast for medical imaging, and that the membrane may be tensioned with a mechanical device or by means of an inflatable bladder. U.S. Pat. No. 6,587,578 discusses a non-rigid object holder comprising a resilient membrane attached to a first member to form an inflatable component for holding the object to be examined between the inflatable component and a base support.

Commonly assigned U.S. Pat. Nos. 7,489,761 and 7,792,244 describe (1) placing a fluid-filled pillow or bag between the compression paddle and the breast before the breast is compressed, (2) compressing the breast with a sheet of a material such as Mylar stretched or at least supported between two rods or rollers (instead of using a conventional compression paddle), and (3) using a paddle provided with a lining of concave compressible material.

All of the patents and applications identified above are hereby incorporated by reference in this patent specification as though they are fully set forth herein.

While at least some of the systems mentioned above are believed to have advantageous features, it is believed that a need still remains to further improve breast imaging and patient comfort. This patent specification is directed to new approaches to address challenges in breast imaging and particularly x-ray breast imaging.

One non-limiting example of such new approaches in mammography and/or breast tomosynthesis involves the use of a specially adapted device to control, distribute and re-direct breast compression forces. Preferably, the device comprises an inflatable jacket for the compression paddle.

In a non-limiting example, an x-ray breast imaging system that uses the new approach comprises a data acquisition unit in which an x-ray source selectively emits an imaging x-ray beam, an image receptor receives the beam and produces x-ray imaging information in response thereto, and a breast immobilizer that is between the source and the receptor. The immobilizer comprises a breast platform configured to support a patient's breast for imaging with said beam and a compression paddle supported for movement toward the breast platform to compress the breast and away from the breast platform to release the breast. The compression paddle has a front wall configured to be adjacent the patient's chest wall when the patient's breast is supported for imaging, side walls extending transversely to the front wall, and an underside facing the breast platform. A paddle jacket is removably secured to the compression paddle. Typically, the jacket has a double thickness bottom that extends along the underside of the paddle when secured to the paddle and forms an inflatable chamber. A fluid conduit extends from the chamber to a device to inflate the chamber. Typically, there is a quick-attach coupling between the conduit and the chamber, so that the chamber can be in fluid-flow communication with a fluid control unit that selectively supplies fluid to the chamber to selectively inflate the chamber. An image processor coupled with the image receptor is configured to receive imaging information and produce x-ray images. A workstation and system control unit is configured to control system operations thereof in response to operator inputs.

The compression paddle jacket typically has front and side walls extending along the front and side walls of the compression paddle, respectively, and can be releasably secured to the compression paddle in any one of a number of different ways. In one example, one or more of the jacket's front and side walls comprise clipping members configured to releasably clip upper portions of one or more of the front and side walls of the compression paddle. In another example, the jacket's bottom and, if desired, the front and side walls as well, adhesively adhere to the compression paddle. An exterior portion of one or more of the front wall and bottom of said jacket can include a friction-enhancing surface configured to enhance friction with the patient's skin. The friction enhancing surface can comprise a surface with a sticky substance therein or thereon.

The jacket bottom preferably is substantially transparent to visible light, whereby a technician adjusting a patient's breast for imaging can visualize the breast through said jacket. A non-limiting example of jacket material is vinyl. The jacket bottom can include markings of a material that attenuates the x-ray beam sufficiently to make the markings visible or at least detectable in said x-ray images. The jacket's inflatable chamber in divided into two or more sub-chambers that are inflatable to different pressures. In one example, the jacket can be made of two layers of flexible sheet material that are seamed at least at a portion that extends along a junction between the front wall and the underside of the compression paddle.

In one example of breast imaging, a technician secures the inflatable jacket to the compression paddle and makes a connection between the jacket chamber and a fluid conduit. With the patient's breast on the breast platform, the technician lowers the paddle to compress the breast while manipulating breast tissue, and inflates the jacket's chamber to a pressure that achieves a desired compression and spreading of breast tissue. The immobilized breast is imaged in the desired imaging mode. Typically, a new paddle jacket is used for each patient, so the technician disconnects the fluid flow connection and disposes of the used jacket. The inflation and deflation can be operator-powered, such as by a hand or foot operated pump, with appropriate operator-controlled valves, or powered under operator control using suitable electric or other pumps controlled by buttons or other interface devices or under computer control triggered by the operator or by positioning the paddle relative to the breast (e.g., inflating when the paddle has reached a certain position or acts on the breast with w certain force).

DETAILED DESCRIPTION OF PREFERRED EMBODIMENTS

Figure 1:
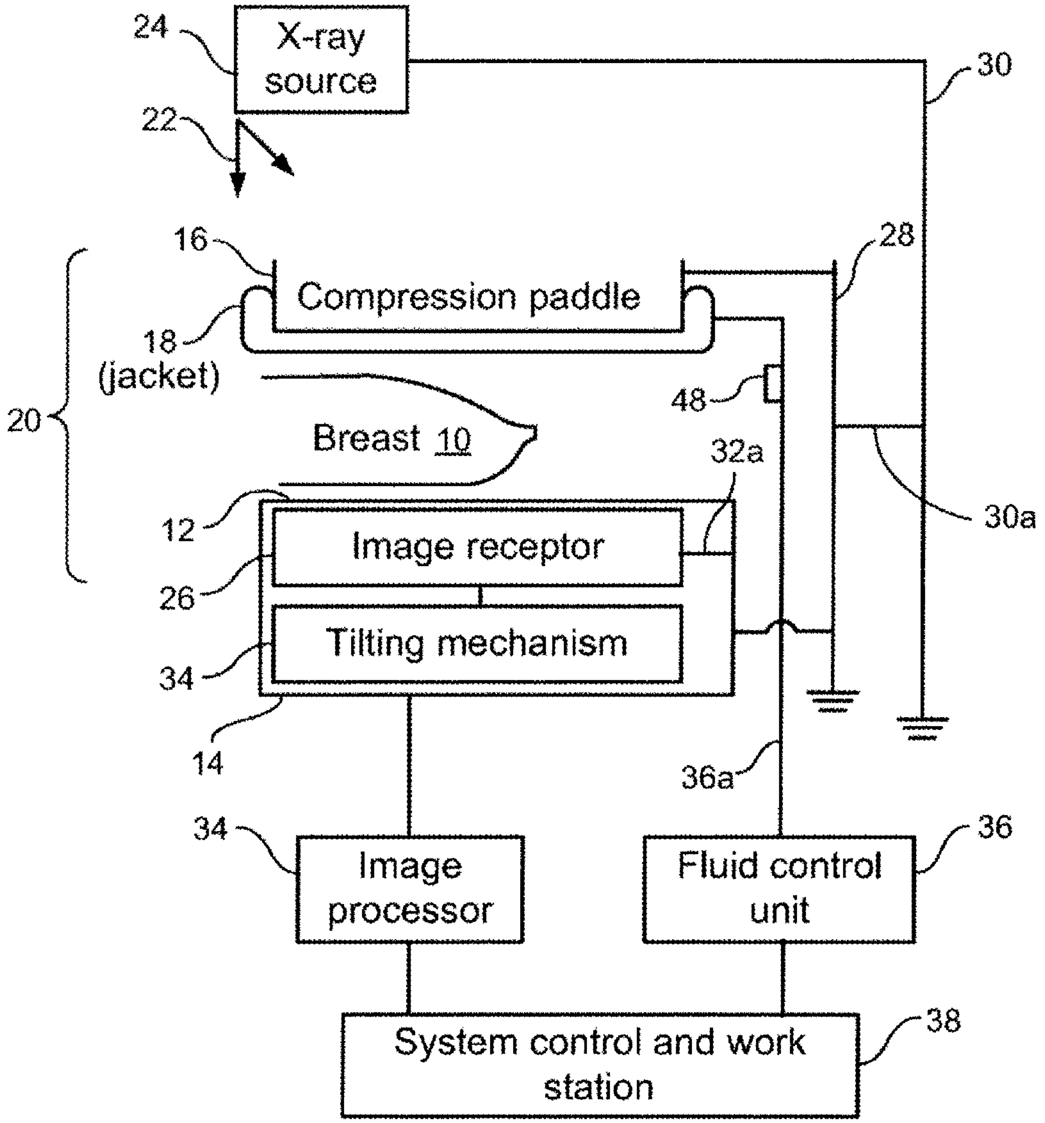
FIG. 1 is a partly schematic view and partly a block diagram of a mammography and/or tomosynthesis system using an inflatable or inflated paddle jacket in imaging a patient's breast with x-rays.
Figure 2:
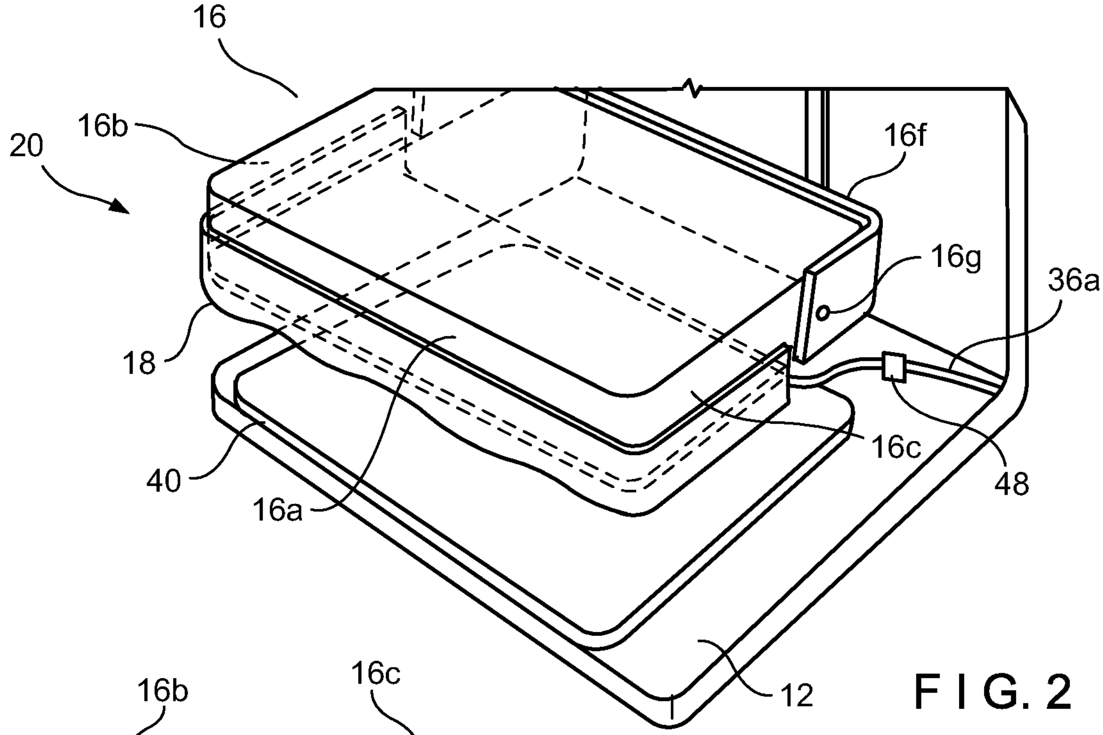
FIG. 2 is a partial perspective view, not to scale, which illustrates a compression paddle provided with an inflatable or inflated jacket and a breast platform with a compressible mat thereon, as a part of an x-ray mammography and/or tomosynthesis system.

Referring to FIG. 1, a patient's breast 10 is immobilized for x-ray imaging between a breast platform 12 and a compression paddle 16. Platform 12 can be the upper surface of a housing 14. At least an underside of compression paddle 16 is covered with an inflatable paddle jacket 18. Platform 12 and paddle 16 form a breast immobilizer unit 20 that is in a path of an imaging beam 22 emanating from x-ray source 24. Beam 22 impinges on image receptor 26 that is in housing 14. Immobilizer 20 and housing 14 are supported on an arm 28. X-ray source 24 is supported on an arm 30. For mammography, support arms 28 and 30 can rotate as a unit about an axis such as at 30*a* between different imaging orientations such as CC and MLO, so that the system can take a mammogram projection image Mp at each orientation. Image receptor 26 remains in place relative to housing 14 while an image Mp is taken. Immobilizer 20 releases breast 10 for movement of arms 28 and 30 to a different imaging orientation. For tomosynthesis, support arm 28 stays in place, with breast 10 immobilized and remaining in place, while at least source support arm 30 rotates source 24 relative to immobilizer 20 and breast 10 about an axis such as 30*a*. The system takes plural tomosynthesis projection images of breast 10 at respective angles of beam 22 relative to breast 10. Concurrently, image receptor 26 may be tilted relative to breast platform 12 in sync with the rotation of source support arm 30. The tilting can be through the same angle as the rotation of course 24, but preferably is through a different angle, selected such that beam 22 remains substantially in the same position on image receptor 26 for each of the plural images Tp. The tilting can be about an axis 32*a*, which can but need not be in the image plane of image receptor 26. A tilting mechanism 34, which also is in housing 14 or is otherwise coupled with receptor 24, can drive image receptor 24 in a tilting motion. Axes 20*a*, 24*a* and 26*a* extend left-right as seen in FIG. 1, and may but preferably do not coincide. For tomosynthesis imaging, breast platform 12 can be horizontal or can be at an angle to the horizontal, e.g., at an orientation similar to that for conventional MLO imaging in mammography. The system of FIG. 1 can be solely a mammography system, or solely a tomosynthesis system, or a "combo" system that can perform both mammography and tomosynthesis imaging. An example of such a combo system has been offered by the assignee hereof under the trade name Selenia Dimensions.

When the system is operated, image receptor 26 produces imaging information in response to illumination by imaging beam 22, and supplies it to image processor 34 for processing to generate breast x-ray images. A fluid control unit 36 connects with inflatable jacket 18 via conduit 36*a*, preferably through a quick-release snap-on connection 48. A system control and work station unit 38 controls the operation of the system and interacts with a user to receive commands and deliver information including processed-ray images.

Referring to FIGS. 1-6 (which are not to scale) for a more detailed illustration of breast immobilizer 20, compression paddle 16 typically is made of clear plastic and has a front wall 16*a*, a left side wall 16*b*, a right side wall 16*c*, and a bottom wall 16*d* having an underside 16*c*. Side walls 16*b* and 16*c* are supported by a bracket 16*f* that in turn is supported by support arm 28 for up-down movement along arm 28. For tilting relative to breast 10, paddle 16 is secured to bracket 16 with pins 16*g* (only the right pin is visible in FIG. 2) and is spring biased such that as paddle 16 presses against breast 10 the front end of paddle 16 lifts against the biasing force. If desirable, a compressible pad 40 may be placed on platform 12 to increase patient comfort, as in known for system offered by the common assignee. In addition, compression paddle 16 can move left-right as in the current system offered by the assignee under the trade name Selenia Dimensions.

An inflatable jacket 18 is releasably secured to compression paddle 16 and has a front wall 18*a*, a left side wall 18*b*, a right side wall 18*c*, and a bottom 18*d* having a top wall 18*e* facing the underside 16*e* of platform 16 and a bottom wall 18*f*. Bottom 18*d* thus comprises an inflatable chamber formed between walls 18*e* and 18*f* of jacket 18. This chamber 18*d* is in fluid flow communication with fluid control unit 36 via conduit 36*a* so it can be selectively inflated and, if desired, selectively deflated, to a desired pressure. A quick connect-release, snap-on connector 48 facilitates convenient connection of chamber 18*d* to fluid control unit 36 and disconnection from unit 36. If desired the bottom of jacket 18 can be divided into two or more chambers, such as chambers 18*h* and 18*i*, by a partition 18*g*, and separate conduits and connect/disconnect device (not shown) can be provided for each so that the two or more chambers can be inflated to desired pressures that may differ from each other.

Jacket 18 can be releasably secured to paddle 16 in any number of ways such that it can be easily attached and removed from paddle 16 and so that it will not undergo undesirable shifts relative to paddle 16 or the patient's skin while the breast is being immobilized and imaged.

Figure 3:
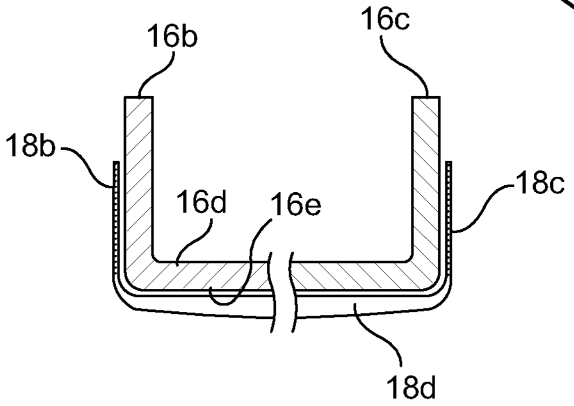
FIG. 3 illustrates schematically a section of the compression paddle with a paddle jacket secured thereto.

FIG. 3 illustrates one example, in which at least some of the surfaces of jacket 18 that face platform 16 are made of or coated with a material that adheres to platform 16 with a force that is sufficiently high to substantially prevent undesirable movement between platform 16 and jacket 18 but also sufficiently low to allow for easy removal of jacket 18 from paddle 16. Preferably at least the upper wall 18*e* of jacket 18 is made sticky for that purpose, but any one or more of the other walls can also be made sticky instead of or in addition to wall 16*c*. In this example of using adhesion to releasably secure jacket 18 to paddle 16, the front and side walls of jacket 18 preferably are shorter than the corresponding walls of paddle 16 but in the alternative can be the same height or even taller. The walls of jacket 18 can but need not be the same height; for example front wall 18*a* can have a lesser height compared with side walls 18*b* and 18*c*.

Figure 4:
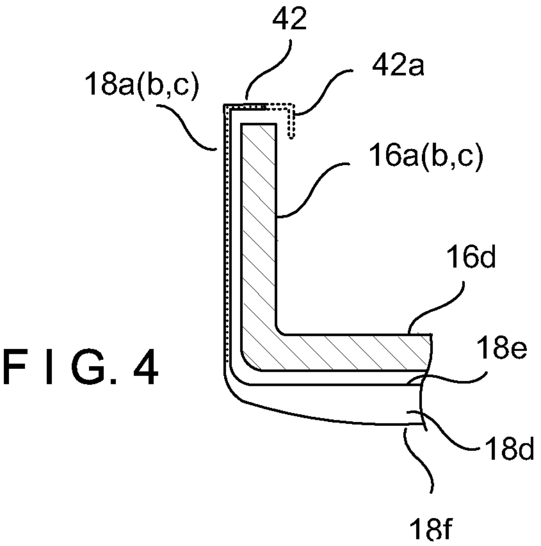
FIG. 4 illustrates schematically two examples of ways to releasably secure a paddle jacket to a compression paddle.

FIG. 4 illustrates other examples of releasably securing jacket 18 to paddle 16. In this example, at least one but preferably two or all three of front wall 18*a* and side walls 18*b* and 18*c* are provided with clipping members 42 that clip over the top of the respective wall of platform 16 and thus keep jacket 18 and platform 16 secured to each other. Clipping member 42 can be as shown in solid lines, or it can have an extension 42*a* as shown in dashed line. Jacket 18 typically is made of a plastic material such as vinyl that is somewhat stretchable and is dimensioned for a tight fit over platform 16 such that mechanical friction and perhaps some electrostatic force and inherent stickiness of the jacket material combine to maintain the jacket and platform from undesirable movement with respect to each other, but jacket 18 can still be easily peeled from paddle 16 by an operator so that a new jacket can be installed for the next patient if desired. Other example are contemplated, such as snap connections between the side walls of the jacket and the compression paddle, or other mechanical connections.

Figure 5:
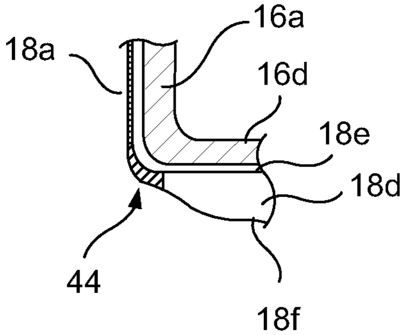
FIG. 5 illustrates schematically a seam in the paddle jacket.

Jacket 18 can be made of two layers of a material such a vinyl similar in chemical composition and thickness to that used for colostomy bags and even kitchen food bags and freezer bags. Preferably the two layers are fused or adhered to each other at the front and side walls of jacket 18, but not at the bottom 18*d* of jacket 18. Preferably, a seam 44 is formed, e.g., with adhesive material or by fusing, joining the two layers where jacket 18 adjoins the junction of the front and underside of platform 16 when jacket 18 is secured to platform 16, as illustrated in FIG. 5. Seam 42 can extend partly over front wall 16*a* and partly over underside 16*e* of platform 16, as illustrated (not to scale) in FIG. 5. Preferably, seam 42 is positioned such that the inflatable volume 18*d* of jacket 18 does not extent forward beyond front wall 16*a* of platform 16, so as not to push patient tissue away from platform 16.

Figure 6:
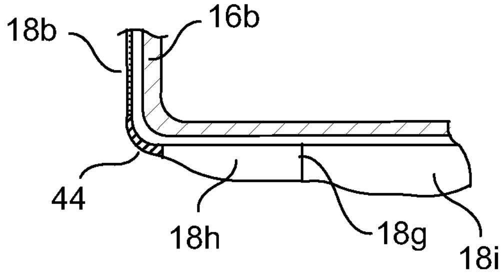
FIG. 6 illustrates a variant in which the bottom of the jacket comprises multiple chambers that can be pressurized to different degrees.

Referring to FIG. 6, the jacket's chamber 18*d* can comprise two or more sub-chambers, such as shown at 18*h* and 18*i*, each with a respective connection through a snap-on connector and a conduit to fluid control unit 36, so that each sub-chamber can be inflated to a desired pressure level under operator control or automated system control.

Fluid control unit 36 can be powered by an operator, using a hand-pump or a foot pump and appropriate manual or foot-controlled valves. Alternatively, electric or fluid-powered pumps can be used, with appropriate valves and interfaces such as buttons or switches that the operator controls. As another alternative, fluid control unit 36 can be fully automated such that inflation/deflation of jacket 18 is under control of station 38, when so enabled by an operator, and in response to events such as compression paddle 16 reaching a certain position relative to the patient's breast or to platform 12 or exerting a specified pressure on the patient's breast. The controls over inflation/deflation can be a part of or at least associated with unit 38.

In use, the mammography and/or tomosynthesis system is operated as known, for example as known for the systems offered by the common assignee under the commercial designations Selenia and Selenia Dimensions, except for the addition of inflatable paddle jacket 18. Thus, before patient imaging, a jacket 18 is secured to paddle 16 and connected to conduit 36 through a snap-on connector 48. With patient's breast 10 on platform 12 or pad 40, the technician lowers paddle 16 (with jacket 18 secured thereto) to begin compressing breast 10, while manually manipulating the breast to spread out breast tissue and pull tissue away from the patient's chest wall and into the x-ray field of view. In this process, the technician may control the degree of inflation of the jacket's chamber 18*d* before and/or after paddle 16 has been lowered to its final desired position by adding to and/or releasing fluid from chamber 18*d*. If chamber 18*d* comprises two or more sub-chambers, the technician may individually control the inflation of each in a similar manner. Once the technician or other health professional is satisfied with the position of breast 10, x-ray imaging can commence in a mammography and/or tomosynthesis mode, for example as known for said systems offered by the common assignee.

Figure 9:
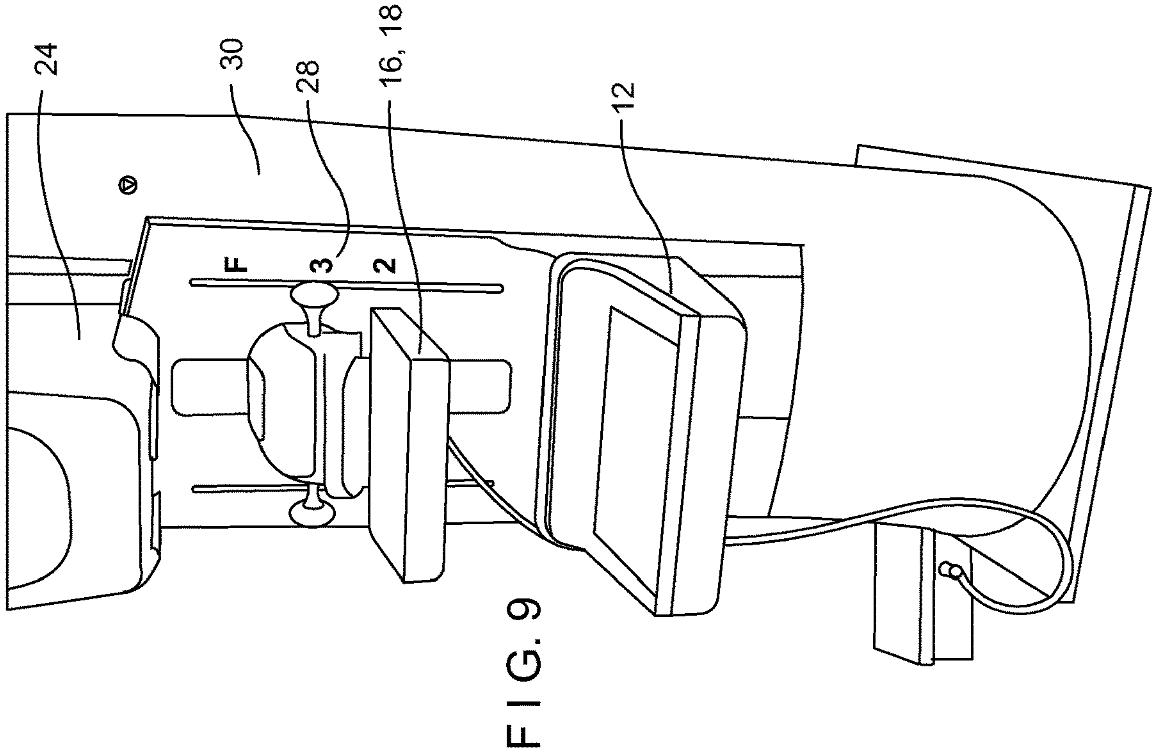
FIG. 9 illustrates a breast imaging system using an inflatable jacket over the compression paddle.
Figure 7:
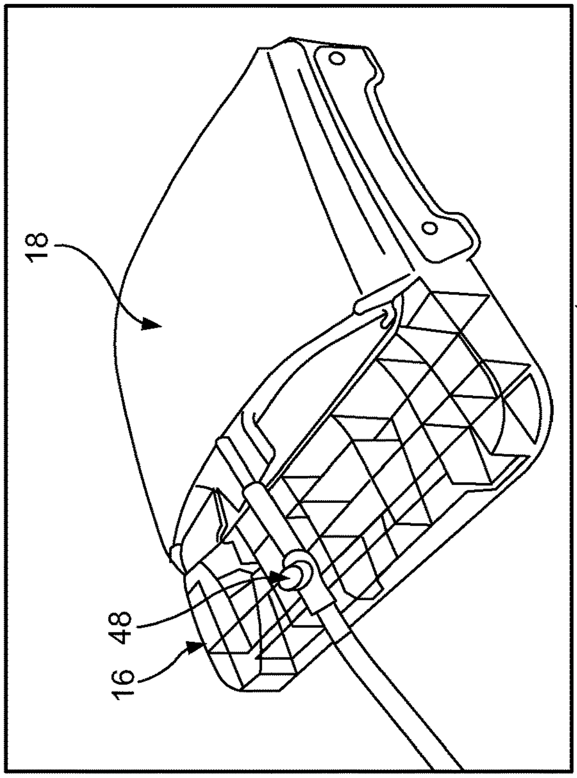
FIG. 7 is a perspective view of an inflatable jacket secured to a compression paddle (upside down).
Figure 8:
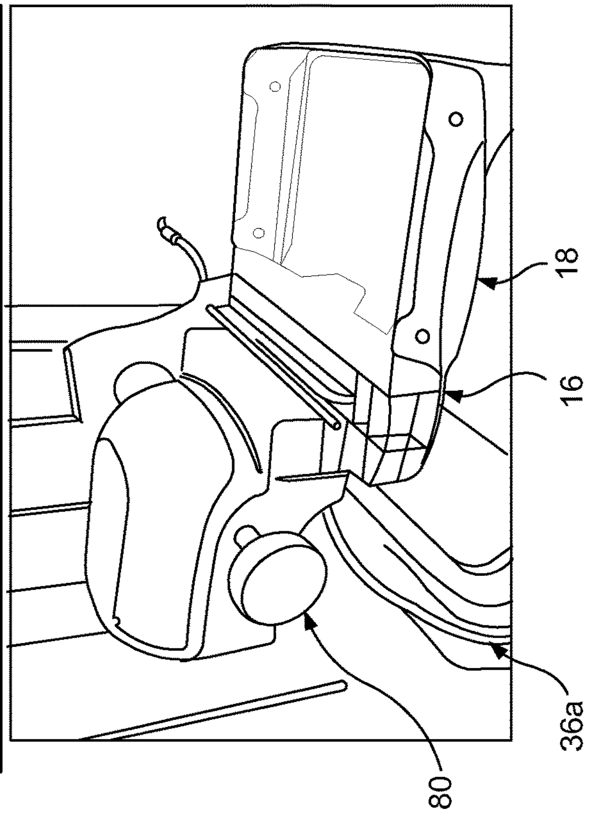
FIG. 8 illustrates a compression paddle with an inflatable jacket secured thereto, and with the combination secured to a breast imaging system.

FIGS. 7-10 illustrate examples of an inflatable or inflated jacket 18 secured to a compression paddle in a breast imaging system. In FIG. 7, jacket 18 and paddle 16 are upside-down to better illustrate them and quick-release coupling 48. FIG. 8 illustrates paddle 16 and jacket 18 in a more typical orientation, and also illustrates a knob 80 that can be manually turned to move paddle 16 and its support left-right. FIG. 9 illustrates in perspective view a system in which components are identified by reference numeral used in FIG. 1 and described in connection with FIG. 1.

While specific examples have been described above, it should be clear that variations thereof are within the scope of the invention defined by the appended claim. As one of many possible examples, a similar inflatable jacket can be used on or over breast platform 12 in addition to or instead of using jacket 18 on compression paddle 16. In that example, such a jacket can be similarly secured to housing 14, or it can omit the side walls so that only a chamber similar to chamber 18*d* (or multiple sub-chambers) is present on breast platform 12, possibly with a front wall similar to front wall 18*a* but extending down along the front wall of housing 14.

The invention claimed is:

1. An x-ray breast imaging system comprising:

a breast platform configured to support a patient's breast for imaging;

a compression paddle supported for movement toward the breast platform to compress the patient's breast;

a paddle jacket removably secured proximate an underside of the compression paddle, the paddle jacket comprising a first inflatable chamber and a second inflatable chamber;

a first fluid conduit that is in fluid flow communication with the first inflatable chamber;

a second fluid conduit that is in fluid flow communication with the second inflatable chamber; and a fluid control unit releasably coupled with the first fluid conduit and the second fluid conduit to selectively inflate the first inflatable chamber and the second inflatable chamber to different pressures.

2. The x-ray breast imaging system of claim 1, wherein the paddle jacket comprises a partition disposed between the first inflatable chamber and the second inflatable chamber.

3. The x-ray breast imaging system of claim 1, wherein the compression paddle comprises a front wall configured to be adjacent a patient's chest wall when the patient's breast is supported for imaging, and the underside of the compression paddle is configured to be adjacent the patient's breast when the patient's breast is supported for imaging.

4. The x-ray breast imaging system of claim 3, wherein the first inflatable chamber is disposed proximate the underside of the compression paddle when the patient's breast is supported for imaging.

5. The x-ray breast imaging system of claim 4, wherein the second inflatable chamber is disposed proximate the underside of the compression paddle when the patient's breast is supported for imaging.

6. The x-ray breast imaging system of claim 3, wherein the first inflatable chamber is disposed proximate a forward portion of the compression paddle when the patient's breast is supported for imaging.

7. The x-ray breast imaging system of claim 6, wherein the second inflatable chamber is disposed proximate a rearward portion of the compression paddle when the patient's breast is supported for imaging.

8. The x-ray breast imaging system of claim 1, wherein the paddle jacket comprises two layers of flexible sheet material, the two layers of flexible sheet material coupled together to form a seam, the seam positioned at least partially along a junction between a front wall and the underside of the compression paddle.

9. The x-ray breast imaging system of claim 8, wherein the paddle jacket further comprises a clipping member configured to releasably clip the seam to the front wall of the compression paddle.

10. A method of imaging a breast with x-rays emitted from an imaging system comprising:

supporting the breast on a breast platform of the imaging system;

compressing the breast with a compression paddle having a paddle jacket removably secured proximate an underside of the compression paddle, the paddle jacket including a first inflatable chamber and a second inflatable chamber;

inflating the first inflatable chamber to a first pressure via a first fluid conduit in fluid flow communication with the first inflatable chamber;

inflating the second inflatable chamber to a second pressure via a second fluid conduit in fluid flow communication with the second inflatable chamber; and controlling, via a fluid control unit releasably coupled to the first fluid conduit and the second fluid conduit, the first pressure and the second pressure such that the pressures are different.

11. The method of claim 10, wherein the first inflatable chamber and the second inflatable chamber are separated by a partition such that inflation of the first inflatable chamber is independent from inflation of the second inflatable chamber.

12. The method of claim 10, wherein compressing the breast with the compression paddle includes positioning a front wall of the compression paddle adjacent a patient's chest wall.

13. The method of claim 12, wherein the first inflatable chamber is disposed proximate the underside of the compression paddle during breast compression.

14. The method of claim 13, wherein the second inflatable chamber is disposed proximate the underside of the compression paddle during breast compression.

15. The method of claim 12, wherein the first inflatable chamber is disposed proximate a forward portion of the compression paddle during breast compression.

16. The method of claim 15, wherein the second inflatable chamber is disposed proximate a rearward portion of the compression paddle during breast compression.

17. The method of claim 10, further comprising providing the paddle jacket having two layers of flexible sheet material, the two layers of flexible sheet material coupled together to form a seam, the seam positioned at least partially along a junction between a front wall and the underside of the compression paddle.

18. The method of claim 17, further comprising releasably coupling the paddle jacket to the compression paddle, the paddle jacket including a clipping member that releasably clips the seam to the front wall of the compression paddle.

19. An x-ray breast imaging system comprising:

a breast platform configured to support a patient's breast for imaging;

a compression paddle supported for movement toward the breast platform to compress the patient's breast, the compression paddle having a front wall configured to be adjacent a patient's chest wall when the patient's breast is supported for imaging, and an underside configured to be adjacent the patient's breast when the patient's breast is supported for imaging; and a paddle jacket removably secured to the compression paddle, the paddle jacket comprising:

an inflatable chamber disposed between the compression paddle and the patient's breast when the patient's breast is supported for imaging; and a seam disposed (a) between the front wall and the patient's chest wall when the patient's breast is supported for imaging, and (b) between the underside and the patient's breast when the patient's breast is supported for imaging.

20. The x-ray breast imaging system of claim 19, wherein the paddle jacket further comprises a clipping member configured to releasably clip the seam to the front wall of the compression paddle.

* * * * *